Figure 1:
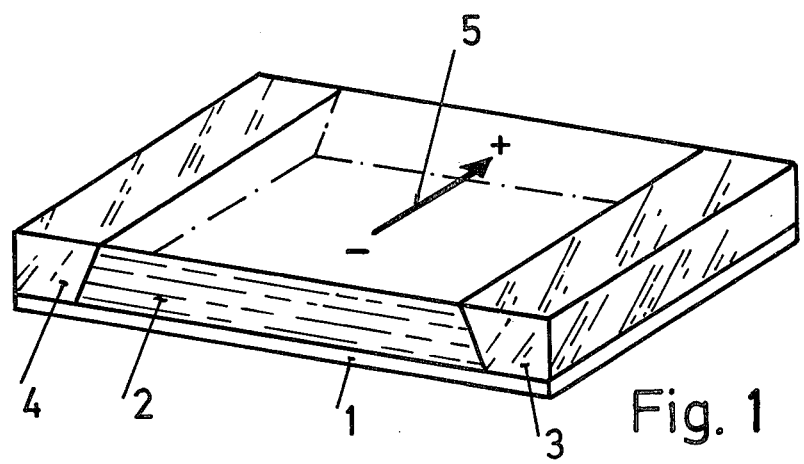

United States Patent [19]

Denckla

[11] 4,194,963
[45] Mar. 25, 1980

[54] ELECTROPHORESIS APPARATUS

[76] Inventor: W. Donner Denckla, 405 Commonwealth Ave., Newton Ctr., Boston, Mass.

[21] Appl. No.: 957,222

[22] Filed: Nov. 2, 1978

[30] Foreign Application Priority Data

Nov. 4, 1977 [SE] Sweden .................................. 7712499

[51] Int. Cl.² .............................................. G01N 27/28
[52] U.S. Cl. ............................ 204/299 R; 204/180 R
[58] Field of Search ................... 204/299 R, 300, 301, 204/180 R, 180 S, 180 G; 424/12; 23/230 B

[56] References Cited

U.S. PATENT DOCUMENTS

| 3,208,929 | 9/1965 | Raymond et al. | 204/299 R |
| 3,616,456 | 10/1971 | Valmet | 204/299 R |
| 3,902,987 | 9/1975 | Canley | 204/299 R |
| 3,962,058 | 6/1976 | Denckla | 204/180 R |

Primary Examiner—Arthur C. Prescott
Attorney, Agent, or Firm—Fisher, Christen & Sabol

[57] ABSTRACT

A vessel to be used to contain an electrophoresis medium is provided with electrically non-conductive side walls whose thickness vary between a minimum adjacent to the cooled bottom of the vessel and a maximum at a level spaced from the bottom wall so as to reduce the transverse curvature of the electrophoresis bands when an electric potential is applied between the respective ends of the vessel.

4 Claims, 6 Drawing Figures

ELECTROPHORESIS APPARATUS

The present invention relates to an electrophoresis apparatus provided with two end walls each bearing an electrode device, two side walls and a cooled bottom wall, the walls and the bottom forming a chamber intended to contain a conducting medium.

One of the great problems with all electrophoresis configurations is the tendency of the compounds being separated to distribute themselves in a non-parallel manner in respect to the electrodes. The substance layers have thus the tendency of curving at the edge of the electrophoresis vessel. Often the curvature at the edge of the vessel becomes so marked that it makes difficult a desired separation of the compounds. The problem applies equally well to all electrophoresis media (all conducting media utilized in electrophoresis) such as liquid solutions held in a trough or to solutions contained within some stationary porous material such as for example polyacrylamide gels, sephadex gels, starch or the like. The problem is also applicable in various systems for isoelectric focusing.

The phenomenon described above is due to the fact that the cooling at the edge of the electrophoresis vessel is poorer than in the middle of it. Since most ionic solutions at the temperatures in question unlike most metals, have an increase in conductance with increasing temperature, a positive feedback is obtained, i.e. as the temperature at the edge of the electrophoresis vessel rises compared to the temperature of the main part of the vessel, due to the relatively poor cooling, the solution at the edge becomes more conductive. The increase in conductivity causes a greater current flow in this area of the medium and this naturally results in even further heating of the edge. This can eventually result, in extreme cases, in a situation where virtually all the power applied to the vessel is being dissipated in two narrow zones near the edge with the resulting extreme curvature of the electric field and corresponding curvature of the distribution of the compounds one is trying to separate with electrophoresis. This effect has been observed in isoelectric focusing in acrylamide, and sephadex gels and in simple water solutions held in troughs of various length to width ratios and various thicknesses. The phenomenon has also been observed in acrylamide gel electrophoresis using conventional buffer systems. Temperature measurements have confirmed that, in an area a few millimeters from the edge of the vessel, temperatures can be obtained which exceed the temperature in the main body of the vessel with as much as 7° C.

An object of the present inveniton is therefore to provide an electrophoresis apparatus in which the cooling problem mentioned above is eliminated. The characteristics of the invention are described in the claims attached to the specification.

Figure 2:
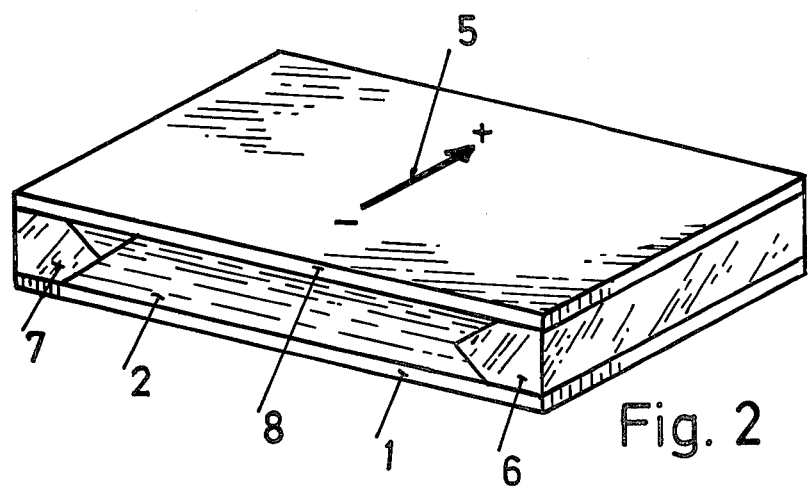

The invention will now be further explained, reference being made to the attached drawing in which:

FIG. 1 schematically shows a first embodiment of an electrophoresis apparatus according to the invention;

FIG. 2 schematically shows a second embodiment of an electrophoresis apparatus according to the invention;

FIGS. 3-6 schematically show the effects that can be obtained by utilizing the device according to the invention.

In FIG. 1, reference 1 denotes the cooled bottom wall in an electrophoresis vessel. The cooling is suitably performed by providing the bottom wall with a cavity through which a cooling medium, e.g. water, is being pumped. Furthermore, the electrophoresis vessel is provided with two side walls 3 and 4 made of an electric isolating material, for example glass or plastic. According to the invention these side walls are thereby so formed that they have a wedge shaped sectional area. The electrophoresis vessel contains an electrophoresis medium 2 in which the electrophoretic separation is carried out in the way that a voltage is applied to the medium from two electrode devices not shown in the figure. The electrophoresis direction is thereby marked with the arrow 5.

In FIG. 2 is shown a second application of the electrophoresis apparatus according to the invention, the latter differing from the one shown in FIG. 1 thereby that it is also provided with a top cooling surface 8 and the electric isolating side walls 6 and 7 have a sectional area which is symmetrically wedge shaped in relation to the two cooling surfaces.

In the devices shown in FIGS. 1 and 2 by means of the wedge shaped side walls the result is that the total current flow at the side walls decreases, the decrease obviously being dependant on how far the wedge protrudes into the medium. In practice, it has been found that in devices according to FIG. 1, suitably a top angle for the wedge of 45 to 60 degrees, preferably about 45 degrees, may be used, while in devices according to FIG. 2 the top angle of the wedge ought to be 45 to 60 degrees, preferably about 60 degrees.

Figure 3:
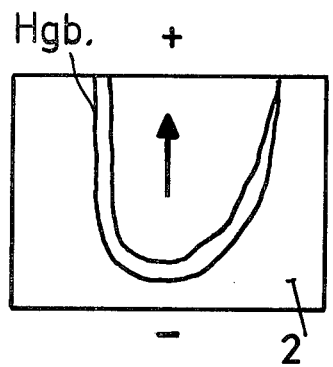
Figure 4:
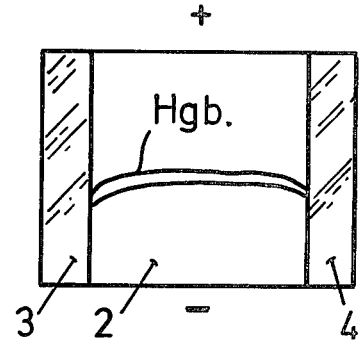
Figure 5:
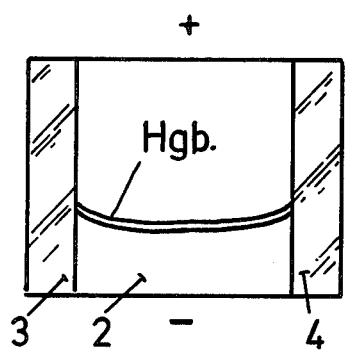
Figure 6:
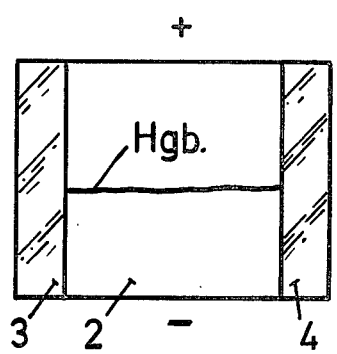

The devices shown in FIGS. 1 and 2 have been tested by protein separation in a 1 cm thick acrylamide gel operating under conditions of isoelectric focusing. In some cases the wedge has thereby performed such an effective cooling at the edge that the protein bands have reversed in direction compared to what is normally the case. This can, however, be compensated by an increase of the current flow. In the same way, if the curvature of the bands is not fully eliminated by means of the wedge shaped walls, one can minimize the voltage effect so that the bands become parallel to the electrode walls. This is however impossible without the use of wedge shaped walls as in such case one is obliged to minimize the current effect so that the separation takes unreasonable long time. The process thus described is illustrated in FIGS. 3-6 which show the hemoglobin band (Hgb) in a protein separation, FIG. 3 showing the band without the use of wedge shaped side walls, FIG. 4 showing the band with the use of walls but with too low current flow, FIG. 5 showing the same separation with too high current flow and FIG. 6 showing the separation at a well balanced current flow.

The present invention thus relates to an improved electrophoresis apparatus, the apparatus being provided with wedge shaped side walls made of a non-conductive material, the minimum transverse width of such wall being adjacent to the cooled surface or surfaces and the maximum transverse width being at the point remote from said surfaces. In such a way it is possible to eliminate the curvatures of the electrophoresis bands at the edge of the electrophoresis vessel which otherwise always occur.

We claim:

1. Electrophoresis apparatus provided with two end walls each bearing an electrode device, two side walls and a cooled bottom wall, the walls and the bottom forming a chamber intended to contain a conductive medium, characterized in that said side walls are wedge shaped and made of an electric non-conductive material the minimum transverse width of the wall being adjacent to the cooled bottom wall and the maximum transverse width at the point remote from said bottom wall.

2. Electrophoresis apparatus according to claim 1, characterized in that the top angle of the wedge is about 45 degrees.

3. Electrophoresis apparatus according to claim 1, characterized in that the apparatus is also provided with a cooled top surface, the maximum transverse width of the side walls being located at the vertical mid point between the top wall and the bottom wall.

4. electrophoresis apparatus according to claim 3, characterized in that the top angle of the wedge is about 60 degrees.

* * * * *